United States Patent
Demmitt et al.

(10) Patent No.: US 11,666,882 B2
(45) Date of Patent: Jun. 6, 2023

(54) BIDIRECTIONAL FLOW REACTION SYSTEM FOR SOLID PHASE SYNTHESIS

(71) Applicant: Biolytic Lab Performance, Inc., Fremont, CA (US)

(72) Inventors: Thomas J. Demmitt, Fremont, CA (US); Laurent Jaquinod, Davis, CA (US)

(73) Assignee: Biolytic Lab Performance, Inc., Fremont, CA (US)

( * ) Notice: Subject to any disclaimer, the term of this patent is extended or adjusted under 35 U.S.C. 154(b) by 124 days.

(21) Appl. No.: 17/359,021

(22) Filed: Jun. 25, 2021

(65) Prior Publication Data
US 2021/0402364 A1 Dec. 30, 2021

Related U.S. Application Data

(60) Provisional application No. 63/102,684, filed on Jun. 26, 2020, provisional application No. 63/102,680, filed on Jun. 26, 2020.

(51) Int. Cl.
*B01J 19/00* (2006.01)
*B01J 19/24* (2006.01)

(52) U.S. Cl.
CPC ......... *B01J 19/0046* (2013.01); *B01J 19/246* (2013.01); *B01J 2219/00162* (2013.01);
(Continued)

(58) Field of Classification Search
CPC .. B01J 19/0046; B01J 19/2405; B01J 19/246; B01J 2219/00351; B01J 2219/00477; B01J 2219/00164; B01J 2219/00162
See application file for complete search history.

(56) References Cited

U.S. PATENT DOCUMENTS

| 4,517,338 A | * | 5/1985 | Urdea | C07H 21/00 435/317.1 |
| 5,368,823 A | | 11/1994 | McGraw et al. | |

(Continued)

OTHER PUBLICATIONS

Printout: "AKTA Oligopilot plus Operating Instructions", 28-9597-48AC, Mar. 2, 2015, 77 pages.
(Continued)

*Primary Examiner* — Lessanework Seifu
(74) *Attorney, Agent, or Firm* — Mark Protsik; Thomas Schneck

(57) ABSTRACT

Flow control mechanisms control the direction and flow rate of synthesis reagent through one or more synthesis reaction vessels for automated solid phase synthesis. Selectable, known, and reproducible positive or negative pressure differentials (−5 to +10 psi) accomplish controlled, bidirectional (forward and reverse) flow of synthesis reagents through synthesis media contained within the reaction vessels. Venturi-based vacuum apparatus, valves, electronic pressure regulators and compound digital pressure gauge, can be added to automated solid phase synthesis instruments to provide, control, and monitor known, selectable, reproducible negative and positive pressures to one or both valve sealable and un-sealable ends (inlets and outlets) of the reaction vessel as needed to generate and reverse said pressure differentials between the opposite ends of said synthesis reaction vessels, yielding controlled forward and backward flows of synthesis reagents through the synthesis media.

22 Claims, 3 Drawing Sheets

(52) U.S. Cl.
CPC ............. *B01J 2219/00164* (2013.01); *B01J 2219/00166* (2013.01)

(56) References Cited

U.S. PATENT DOCUMENTS

| | | |
|---|---|---|
| 5,472,672 A | 12/1995 | Brennan |
| 5,750,881 A | 5/1998 | Dorenkott et al. |
| 5,792,430 A * | 8/1998 | Hamper ............... B01J 19/0046 422/138 |
| 5,869,643 A | 2/1999 | Chatelain et al. |
| 5,964,254 A * | 10/1999 | Jackson ................. F17C 13/04 141/59 |
| 6,270,730 B1 | 8/2001 | McLuen et al. |
| 7,691,316 B2 | 4/2010 | Ngo et al. |
| 8,361,396 B2 | 1/2013 | Parker et al. |
| 9,069,358 B2 | 6/2015 | Demmitt |
| 2013/0177490 A1* | 7/2013 | Richardson ............ B01D 53/60 423/235 |
| 2017/0354847 A1* | 12/2017 | Carter .................... A63B 27/00 |
| 2019/0076814 A1* | 3/2019 | Dabrowski ........ C12N 15/1093 |

OTHER PUBLICATIONS

S.Rayner et al., "MerMade: An oligodeoxyribonucleotide synthesizer for high throughput oligonucleotide production in dual 96-well plates", Genome Research, Cold Spring Harbor Laboratory Press ISSN 1054-9803/98, Jul. 1998, 8:741-747.

L.Sindelar et al., "High-throughput DNA synthesis in a multichannel format", Nucleic Acids Research, Mar. 1995, vol. 23, No. 6, 1995 Oxford University Press, pp. 982-987.

* cited by examiner

BIDIRECTIONAL FLOW REACTION SYSTEM FOR SOLID PHASE SYNTHESIS

CROSS-REFERENCE TO RELATED APPLICATION

This application claims priority under 35 U.S.C. 119(e) from U.S. provisional application No. 63/102,684, filed on Jun. 26, 2020, titled "High throughput synthesizers with oscillating pressure differentials and method of use", and U.S. provisional application No. 63/102,680, filed on Jun. 26, 2020, titled "Low to Medium throughput synthesizers featuring double-acting cylinder-based mixing pumps and methods of use".

TECHNICAL FIELD

The invention relates to fluid flow mechanisms in synthesizers and in particular, to selectable, known, reproducible control of flow rate and flow direction through synthesis reaction vessels used in automated solid phase synthesis.

BACKGROUND ART

Achieving efficient and complete reaction is a critical requirement in the successful performance of automated solid phase synthesis. Automated solid phase synthesis is commonly used for but not limited to the synthesis of oligomers such as peptides, peptide analogues and notably nucleic acids (such as synthetic DNA, RNA, Locked Nucleic Acids (LNA), Peptide Nucleic Acids, modified DNA or modified RNA).

Solid phase synthesis involves exposing a derivatized synthesis medium packed in flow-through synthesis reaction vessels to liquid synthesis reagents containing a large molar excess of reactants where the reactants will react with active sites on the synthesis medium. Volumes of reagents used in automated solid phase synthesis such as nucleic acid synthesis, per cycle for a given synthesis scale, have little varied in current automated solid phase synthesizers from early designs. This is due to the limiting design of the reaction system used in current automated synthesis systems which uses unidirectional flow of liquid reagents through the synthesis media. Inherent in unidirectional flow design, reactants that could still participate in the reactions taking place with the synthesis media end up in the waste container once the reactants have flowed past the synthesis media. Also inherent in unidirectional designs where parallel synthesis is performed in many synthesis reaction vessels simultaneously, achieving the same flow rates of reagents through parallel reaction vessels is desired but almost impossible. These systems require delivering larger volumes of reagents to compensate for reaction vessels flow rate differences to ensure all reaction vessels achieve the same level of reaction completion.

The practice of recirculating liquid reagents in synthesis reaction vessels is known from loops disclosed in the prior art where pumps, check valves, actuated valves, and tubing are used to create a loop for recirculation of synthesis regents through synthesis medium.

SUMMARY DISCLOSURE

Bidirectional flow is established for reacting reactants contained in one or more synthesis reagents with reactive sites on synthesis medium where the synthesis medium is contained within synthesis reaction vessels. The bidirectional flow apparatus moves synthesis reagents through reaction vessels in two directions whereby reagents containing unreacted reactants that have flowed through synthesis reaction vessels past the synthesis media are reversed in flow and thereby brought back in contact with the synthesis media thus recycling otherwise wasted reactants. A reaction system that uses the bidirectional flow of the invention can also overcome the reaction vessels flow rate differences common to parallel synthesis.

Methods used in automated solid phase synthesis involve hardware and control systems that follow a user defined, prewritten protocol to automatically dispense one or more liquid reagents to flow-through synthesis reaction vessels where the synthesis reaction vessels contain synthesis medium that allows reactants in liquid reagent to flow through and react with active sites of synthesis medium while keeping the synthesis medium in synthesis reaction vessels. Critical to optimization of solid phase synthesis is the time the synthesis reagents are in contact with the active sites of the synthesis medium in the synthesis reaction vessels.

Bidirectional flow keeps synthesis reagents within the synthesis reaction vessels and eliminates the need for pumps, check valves, tubing external to the synthesis reaction vessels all of which need to be cleaned between chemistry steps. Bidirectional flow of the invention requires only washing the synthesis medium.

Bidirectional flow systems are applicable to current as well as newly designed solid phase synthesizers, adding the possibility to flow known, reproducible volumes of liquid reagents backward, i.e., against gravity, or forward through synthesis reaction vessels. To achieve known, reproducible, forward and backward flows of synthesis reagents, herein called bidirectional flow, conditions to be met are:

(1) a system that can alternately seal and unseal synthesis reaction vessel inlets, as well as seal and unseal synthesis reaction vessel outlets, such that the synthesis reaction vessel inlets and outlets can be both pressurized and vented; (2) a valve controllable positive gas pressure flow path to the synthesis reaction vessel inlets and outlets that allows for introduction of a selectable, known, reproducible positive pressure; (3) a valve controlled vacuum flow path to the synthesis reaction vessel inlets and outlets that allows for introduction of a selectable, known, reproducible negative pressure; (4) a valve controllable vent flow path to the synthesis reaction vessel inlets and outlets that allows for independent controlled venting of synthesis reaction vessel inlets as well as outlets; (5) synthesis reaction vessels where the synthesis reaction vessels have volume space at the inlets to accept synthesis reagent volume dispensed by the automated solid phase synthesizer and have volume space between the bottom of the synthesis medium and the outlets of the synthesis reaction vessels to store synthesis reagents; and (6) volume of outlets of synthesis reaction vessels. Hydrophobicity of a synthesis reaction vessel material and size (ID) of outlets of synthesis reaction vessels are designed to allow retention of synthesis reagents within the space below synthesis medium such that synthesis reagents do not exit the synthesis reaction vessels.

The bidirectional flow method further requires the steps of (a) delivering a specific volume of liquid reagents to the synthesis reaction vessels, (b) selecting and applying a known, reproducible pressure to one end of the synthesis reaction vessels to effect a reagent flow in one direction through synthesis medium, (c) selecting and applying a known, reproducible pressure in the opposite direction to the synthesis reaction vessels to effect a reverse flow of reagents through synthesis medium.

Bidirectional reagent flows of the invention addresses and overcomes some main difficulties of parallel synthesis of multiple oligomers using traditional unidirectional synthesizers, for example, the difficult task of designing synthesis protocols that cater to all reaction vessels when variations of reagents flow rates between synthesis reaction vessels increase proportionally with the increasing number of synthesis reaction vessels. When flow rates between synthesis reaction vessels differ significantly, various exposures of the synthesis media to the reagents needed to drive the reactions to completion will generate lower quality oligomers in some if not all synthesis reaction vessels.

Synthesis data demonstrates a saving in reagents due to an improved efficiency of reagent reaction resulting from bidirectional reagent flow. A key success factor is being able to optimize the efficiency and length of time of contact between reactants and reaction sites. This invention provides a tool to maintain contact between reactants and reaction sites for the desired time duration. Although this invention is disclosed with respect to its preferred application to solid phase synthesis of nucleic acids, it is not limited to such application but is applicable to other solid phase oligomer synthesis.

DETAILED DESCRIPTION

Figure 1:
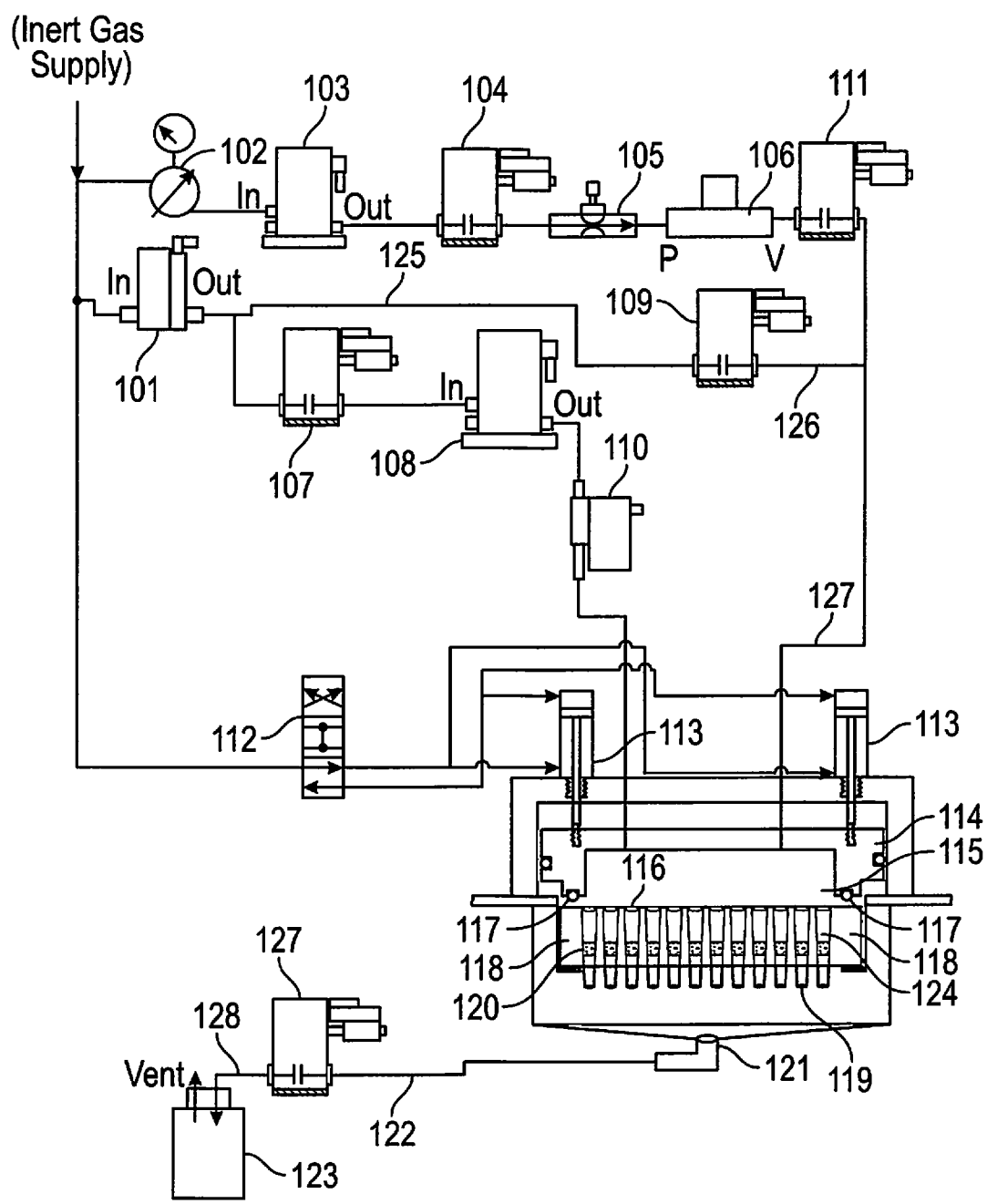
FIG. 1 is a schematic plan view of a first embodiment of a bidirectional reaction flow system for synthesizers having at least one reaction vessel where each reaction vessel has one inlet and where all reaction vessel inlets are located in a common sealable space.

A bidirectional flow reaction system in accord with the present invention may be used in connection with any existing solid phase synthesizer to perform solid phase synthesis chemistry. The bidirectional flow reaction system is not standalone by itself in that it is one part of an overall synthesizer, which has all the other pieces (reagent delivery system, hardware and software control, pneumatics, fluidics, electronics, reagent containment, mechanical systems, and the like according to a synthesizer's specific design) needed to perform the desired synthesis chemistry. The bidirectional flow reaction system of the present invention contains at least one reaction vessel and facilitates bidirectional fluid flow of reagent within and through the reaction vessel or vessels.

Each reaction vessel has two ends. Between the two ends, a reaction vessel contains porous solid synthesis media. The synthesis media is in a fixed location within the reaction vessel so that it does not move under pressures normally applied to either end of the vessel during solid phase synthesis. The synthesis media allows flow of reagent through it in either direction relative to the two ends of the vessel. The synthesis media contains chemically active sites that molecules of interest attach to during synthesis. Reaction vessels used by the present invention have several characteristics that allow the novel bidirectional flow of reagents in those vessels. A first (usually top) end of each reaction vessel contains a space into which to dispense liquid reagent material. A second (usually bottom) end of each reaction vessel contains space with sufficient volume to hold 50% or more of the dispensed reagent volume per reaction. This space at the second end of the reaction vessel, where reagent that has passed through the synthesis media can be stored prior to reversal of the fluid flow direction, has an inner diameter and hydrophobic vessel material properties (e.g., of polypropylene material) that together with surface tension from the reagent forms a seal such that applied low gas pressure pushing the reagent through the synthesis media will not break through the column of synthesis reagent (no aspiration or bubbling through the reagent). The second end of the reaction vessel also has an exit point where spent reagent material can leave the reaction vessel when the desired reaction time duration is complete. This exit point may have a shape different from the (storage) space at the second end of the reaction vessel.

The bidirectional flow reaction system may employ a single reaction vessel or multiple reaction vessels (such as 96-well or 384-well plates). In the case of a single reaction vessel housed by itself, the two ends of the vessel can be independently coupled to devices that control as well as block flow. Therefore, the single vessel can be operated by itself. In the case of multiple reaction vessels, each end of the reaction vessels can be collectively coupled to devices that control as well as block flow through those reaction vessels as a group. The group can have as many reaction vessels as desired, and the reaction vessels can be arranged in any desired physical pattern according to the various synthesizer designs. The multiple reaction vessels can be individually insertable into a holder by a user or can be fixed permanently to each other, as in molded multi-well plates.

The bidirectional flow reaction system facilitates flow of reagent through the reaction vessel or vessels from a first end to a second and then back toward the first end without exiting the second end of the reaction vessels (at least until the full reaction time is complete). The bidirectional fluid flow can be at a steady rate in each direction or can have a variable rate. The flow can stop, wait a time, and then begin again either in the same or opposite direction. In the case of a single reaction vessel housed by itself, the bidirectional flow reaction system operates on that vessel independently of any other reaction vessels that might be part of the synthesizer. In the case of multiple reaction vessels that are independently housed, the bidirectional fluid flow can be applied to one or more of those vessels either independently from one another or simultaneously. In the case of multiple reaction vessels organized in groups with collectively coupled ends, the bidirectional flow is simultaneous within the multiple vessels of a group, but the bidirectional flow can be applied to each group independently of any other group or groups within the same synthesizer, or to one or more of the groups simultaneously.

Bidirectional fluid flow is achieved by creating a net pressure differential between the two ends of a reaction vessel or group of reaction vessels relative to a zero-flow equilibrium pressure differential. The gas pressure differential created results in liquid reagent flowing through the porous solid synthesis media within the reaction vessel or vessels in the direction from net higher pressure to lower pressure ends of the vessels. The rate of fluid flow is controlled by both the amount and rate of change of applied pressure on one or both sides of the vessels, as well as the rate of venting of gas pressure (where venting is used). In each case, when the force applied to a reaction vessel that creates the desired pressure differential is stopped, removed, or vented, the flow of reagent through the synthesis media is consequently slowed or stopped. Thus, fluid flow in either direction can be stopped at any time, and a wait time desired for a reaction can occur. Fluid flow direction may be reversed by reversing the direction of the net pressure differential (from higher at the first end to higher at the second end, and vice versa). Initially, the gas pressure differential is higher at the first end and lower at the second end of a reaction vessel, causing reagent fluid to flow from the first (higher pressure) end to the second (lower pressure) end of the vessel. Then, when gas pressure differential is reversed, so that the pressure becomes higher at the second end than the first end, this reversal causes reagent fluid to now flow from the second end back toward the first end of that reaction vessel.

A variety of pressure differential scenarios are possible, depending on whether positive pressure or negative (vacuum) pressure is applied to either end or both ends, and upon whether any end is left open to atmospheric pressure or sealed or alternately opened and closed:

(1) Second end left open to atmospheric pressure; first end alternately having applied positive and negative pressures;

(2) First end left open to atmospheric pressure; second end alternately having applied negative and positive pressures;

(3) Apply positive gas pressure to first end while second end is left open to atmospheric pressure, then change so that the positive gas pressure is applied to the second end while the first end is open to atmospheric pressure;

(4) Same as (3) but with negative gas pressures; namely apply negative gas pressure to first end while second end is left open to atmospheric pressure, then change so that the negative gas pressure is applied to the second end while the first end is open to atmospheric pressure;

(5) Apply positive gas pressure to the first end while simultaneously applying negative gas pressure to the second end, then switch ends to apply negative gas pressure to the first end while simultaneously applying positive gas pressure to the second end;

(6) Same as (5) but in reverse order, with negative pressure applied initially at the first end and positive pressure at the second end, before reversing;

(7) One end sealed, and the other end alternately with applied positive pressure and controlled venting to atmospheric pressure; namely, apply positive gas pressure at the first end while the second end is closed and has a fluid tight seal; movement of liquid reagent toward the second end causes pressure in the second end to build up until a pressure equilibrium is reached and fluid flow stops; then remove the application of positive gas pressure to the first end and cause controlled venting of the first end; pressure trapped in the sealed second end cause reverse fluid flow from the second end to the first end related to the vent rate in the first end;

(8) Same as (7), but now with the first end sealed and the second end having alternate positive gas pressure and venting.

The bidirectional flow reaction system can have a variety of well-known hardware to create the controlled pressure differentials in the reaction vessels. These may include valves, fluid pressure regulators, fluid flow regulators, pressure gauges or indicators, fluid flow gauges or indicators, vacuum generators, and various mechanical or electronic devices (cylinders, pumps, etc.) for creating positive and/or negative applied gas pressures. Valves with various configurations include, but are not limited to, 2-way normally open, 2-way normally closed, 3-way, 4-way, 5-way, solenoid operated and pneumatically operated valves, as deemed appropriate by those skilled in the solid phase synthesizer art. Fluid pressure regulators and fluid flow regulators of various known designs include, but are not limited to, manually settable, electronically settable, self-contained electronically controllable, and electronically controllable using external close loop feedback components, again as deemed appropriate by those skilled in the art. Pressure gauges or indicators of various known designs include, but are not limited to, analog, digital with external pressure sensor, and digital with built-in pressure sensor, the optimal choice being readily determined by those skilled in the art. Fluid flow gauges or indicator of various known designs include, but are not limited to, analog, digital without external flow sensor, and digital with built-in flow sensor, the optimal choice being readily determined by those skilled in the art. Vacuum generators of various known designs include, but are not limited to, a series of fans mounted in a housing with a sealed inlet and sealed outlet, and a vacuum Venturi generator, where the optimal choice is expected to be readily determined by those skilled in the art. Mechanical and electronic devices for producing positive and negative pressures that can be captured and coupled to ends of the reaction vessels include, but are not limited to, single-acting and double-acting cylinders, diaphragm pumps, peristaltic pumps, piston pumps, and turbine pumps, where again the optimal choice in each situation is readily determinable by those skilled in the solid-phase synthesizer art.

Corresponding methods for using bidirectional fluid flow through one or more reaction vessels are also part of the present invention.

There are various designs of automated solid phase synthesizers which have been and are currently produced. The present invention is designed to be able to be incorporated into suitable existing the automated solid phase synthesizers or into the automated solid phase synthesizers of new designs. A common requirement for successful automated solid phase synthesis is to flow liquid synthesis reagents through a synthesis medium contained in at least one synthesis reaction vessel. The synthesis medium is well defined in the field of solid phase synthesis and can be one or a mix of any number of commonly used synthesis medium such as Controlled Pore Glass (CPG), crossed linked polymeric beads, macroporous polystyrene, gel-like porous beads or magnetic beads sandwiched between two retaining porous filters or medium embedded with ultra-high molecular weight polymers into a porous synthesis frit. Further, the synthesis medium is covalently derivatized with cleavable linkers that are attachment points to allow reactions to take place for synthesis of the desired molecules. The synthesis reaction vessel(s) may be used individually, or a plurality of vessels may be clustered in holders or plates, typically but not limited to 4, 8, 12, 96, 384 or 1536 reaction columns or wells.

In previous art, reagents are moved through the synthesis medium unidirectionally using a pressure differential created by gravity and/or unidirectional pressure or force at a rate that produces a reasonably efficient reaction [(a) Automated synthesis of oligonucleotides, R. A. McGraw, W. M. Grosse, U.S. Pat. No. 5,368,823. (b) MerMade: An Oligodeoxyribonucleotide Synthesizer for High Throughput Oligonucleotide Production in Dual 96-Well Plates, S. Rayner, S. Brignac, R. Bumeiste, Y. Belosludtsev, T. Ward, O'dell Grant, K. O'Brien, G. A. Evans, H. R. Garner, Genome Res. 1998, 8, 741-747. (c) Apparatus and method for polymer synthesis using arrays, T. M. Brennan, U.S. Pat. No. 5,472,672. (d) High-throughput DNA synthesis in a multichannel format. L. E. Indelar, J. M. Jaklevic. Nucleic Acids Res. 1995, 982-987. (e) Automated Polymer Synthesis System, H.-Y. Parker, J. C. Tabone, J. Mulligan, U.S. Pat. No. 8,361,396. (f) Multi-well rotary synthesizer, G. R. Mcluen, R. J. Hanney, D. W. Hugens, U.S. Pat. No. 6,270,730]. When reactions that require a pre-reaction (activation) between two reagents are carried out, a large volume of the first reagent delivered into at least one synthesis reaction vessel is likely to be wasted as first adsorbed by the synthesis medium without mixing and reacting with the second reagent delivered. One way to reduce the need to use larger volume and molar excess of reagent that is required to complete reactions is to direct synthesis reagent flow through a loop system such that the synthesis reagent flows through the synthesis medium multiple times. Looping reagent flow is used by at least one current automated solid phase synthesizer, the AKTA oligopilot having a single or a few synthesis reaction vessels, whereas each active synthesis reaction vessel uses one or more pumps, valves, check valves, and tubing to form a loop, hereafter loop system. While looping reagent flow to pass one or more synthesis reagents through the synthesis medium multiple times using the loop system addresses waste of reactants, it also introduces undesired side effects such as, flowing the synthesis reagents through the loop system multiple times, is time-consuming and requires extensive washing to thoroughly clean the loop system between uses resulting in adding time and increasing consumption of washing reagent. Furthermore, pumps, check valves and valves of the loop system are expensive, require maintenance and can require operational pressures as high as 20 bar (2 MPa). It is an object of the present invention to equip automated solid phase synthesizers with means to keep the positive effects of recirculation of the synthesis reagents while eliminating negative side effects of the existing loop system recirculation of the synthesis reagents through the synthesis reaction vessel (s).

The present invention teaches to use bidirectional flow of the synthesis reagents to move the synthesis reagents, first in one direction (forward) through the synthesis medium, then reversing flow to pass the synthesis reagents in the opposite (reverse) direction through the synthesis medium while keeping the synthesis reagent within the synthesis reaction vessels. Further, the present invention teaches that this process of moving the synthesis reagents forward and reverse (bidirectional synthesis reagent flow) can be performed quickly for mixing and reacting multiple synthesis reagents with each other as well as slowly to allow time for reaction of reactants contained in the synthesis reagent with the synthesis medium. Additionally, the present invention teaches that the process of the bidirectional flow can be repeated as many times as is needed for a chemistry step to go to completion.

The synthesis reagent forward flow followed by reverse flow may are repeated as needed to (a) mix the synthesis reagents to cause the synthesis reagents to react with each other and (b) over as long a time as is needed to drive each chemical reaction to completion.

It is well known in the field of solid phase synthesis the times needed to drive each chemical reaction that is part of the solid phase synthesis chemistry being performed to completion. The invention teaches a bidirectional fluid flow reaction system which can be fitted to automated solid phase synthesizers that can alternately seal and unseal a space containing one or more synthesis reaction vessel inlets, as well as individual synthesis reaction vessel inlets, and/or seal and unseal a separate space containing one or more synthesis reaction vessel outlets, as well as individual synthesis reaction vessel outlets. It is understood that the invention becomes an integrated part of the automated solid phase synthesizer when the invention is fitted to an automated solid phase synthesizer and that the automated solid phase synthesizer will supply the protocols and control systems that are obviously needed to make the invention work within the structure of the automated solid phase synthesizer.

Figure 2:
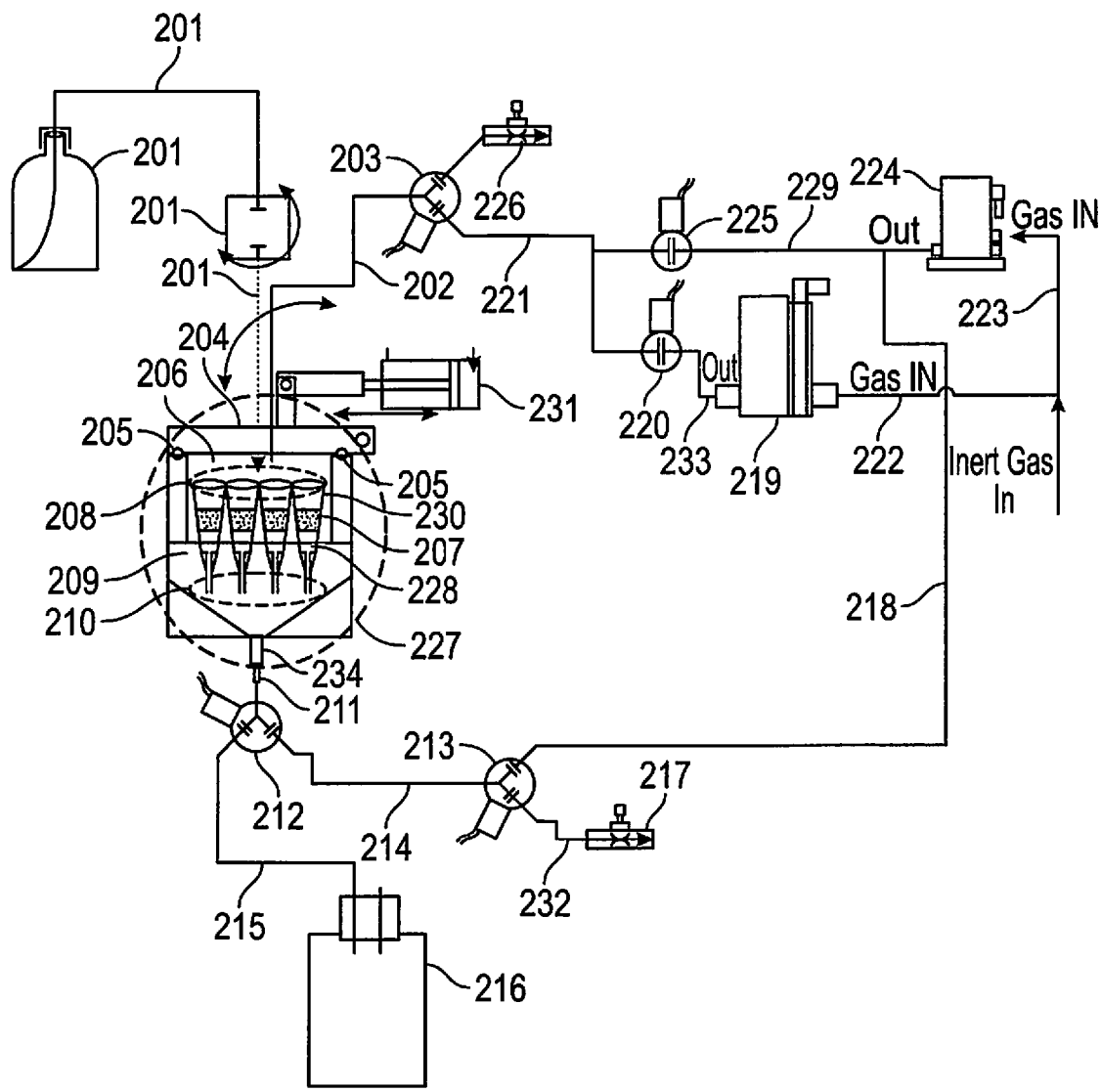
FIG. 2 is a schematic plan view of a second embodiment of a bidirectional reaction flow system for synthesizers having banks containing reaction vessel(s) with their one or more inlets located in a common sealable space and reaction vessel(s) with their one or more outlets in a separate common sealable space.
Figure 3:
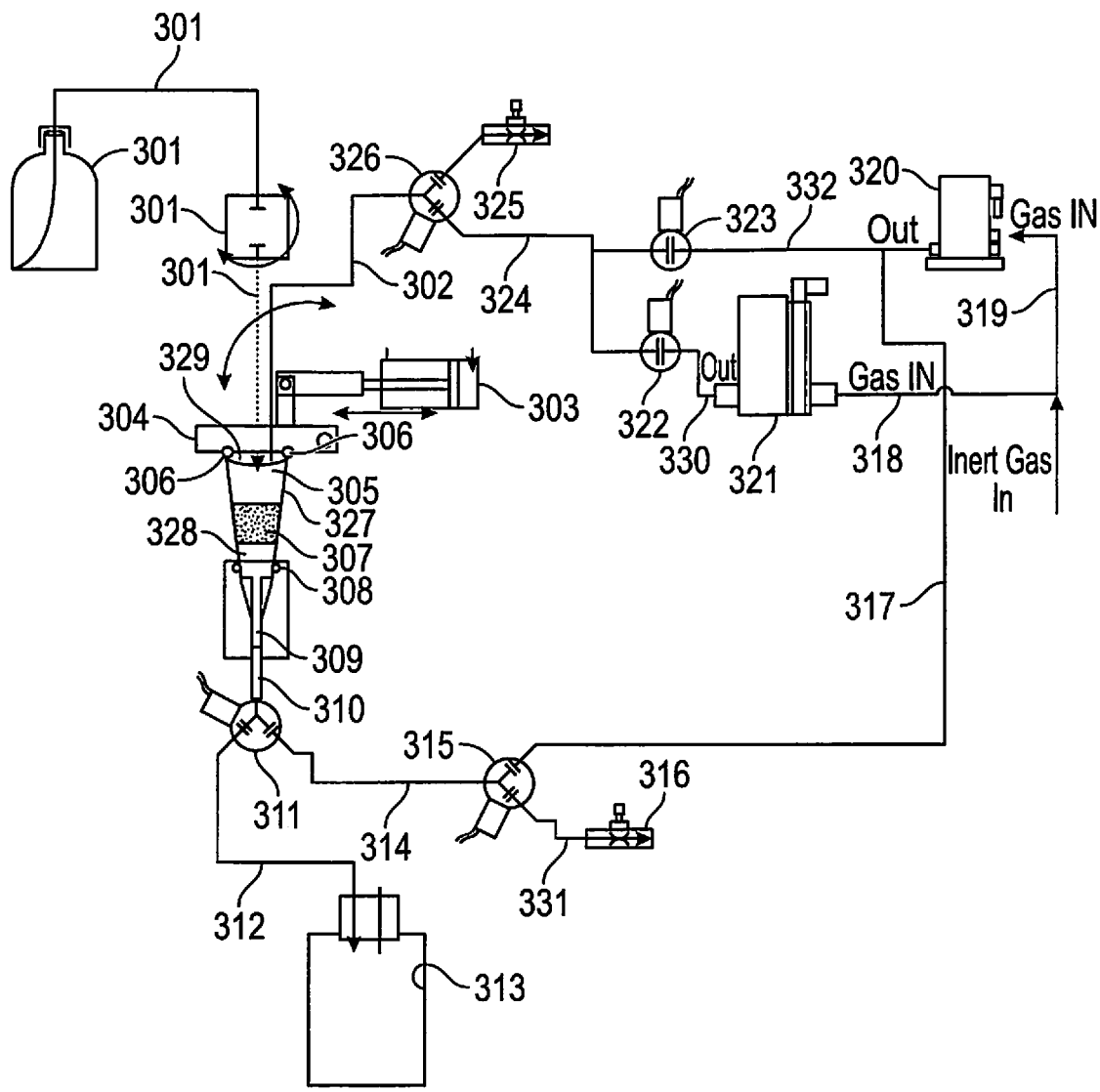
FIG. 3 is a schematic plan view of a third embodiment of a bidirectional reaction flow system for synthesizers having reaction vessel(s) inlet(s) individually sealable and reaction vessel(s) outlet(s) individually sealable.

A bidirectional flow reaction system of the invention creates a means to generate and apply selectable, accurate and reproducible pressure differential(s) in the range of −5 psi to +10 psi (−34 kPa to +69 kPa), in one direction across at least one synthesis reaction vessel, and reversing the pressure differential across the synthesis reaction vessel(s), wherein each synthesis reaction vessel contains a synthesis medium, and whereas one or more synthesis reaction vessel inlets are contained in their own common sealable space and one or more synthesis reaction vessel outlets are contained in their own common sealable space to which the pressure differential is applied to effect movement of reagent material that was introduced into the reaction vessel or vessels to flow in first in one direction through the synthesis medium and then, by reversing the pressure differential across the reaction vessel or vessels, to flow in the opposite direction. When fitting the invention to an automated solid phase synthesizer of designs as shown in FIGS. 1, 2 and 3, all activities described are carried out by the control system of the automated solid phase synthesizer. A preferred embodiment of the invention, whereas the pressure differential is applied to the sealed sealable space containing inlet(s) of the synthesis reaction vessel(s), where the pressure differential is created by applying a selectable, known, reproducible positive pressure or negative pressure to the sealed space containing the inlets of synthesis reaction vessel(s), whereas applying the positive pressure yields a forward direction flow of liquid reagents while applying the negative pressure yields opposite direction flow of liquid reagents through the synthesis medium.

The inlet side in most synthesizers with which the bidirectional flow control system would be used is normally at a top end of the reaction vessel and an outlet side is at a bottom end, with gravity-directed flow inherently from top toward bottom ends even with a neutral pressure differential. Thus, there is a gravity effect on the flow of the synthesis reagent through the porous synthesis media in the reaction vessel(s). The porosity of the synthesis media and the characteristics of each synthesis reagent (density, viscosity, volume) determine the extent of the downward flow rate of the synthesis reagent. In some cases, we use very little downward pressure because of this effect and in the up direction we must overcome this effect. Rather than a neutral pressure differential, an equilibrium pressure differential that is higher at the bottom end would be necessary to have zero flow in such synthesizers. Accordingly, we define the pressure "differential", as used hereafter, as a net pressure relative to the zero-flow equilibrium condition.

FIG. 1 illustrates the embodiment of a Bidirectional synthesis reaction vessel flow system for synthesizers having reaction vessel(s) inlet(s) located in a common sealable space. However, other mechanical designs that result in a system that meets the requirements given in the claims can be used. A reagent delivery system of an automated solid phase synthesizer dispenses reagents into inlets of synthesis reaction vessel(s) 116. A sealable synthesis reaction vessel inlet chamber 115 is formed on the top of the synthesis reaction vessel holder 118 encompassing all inlets 116 of all synthesis reaction vessels in the synthesis reaction vessel holder 118. In this example, the synthesis reaction vessel inlet chamber 115 is sealed by pneumatic cylinders 113 and control valve 112 forcing window assembly 114 with an O-Ring seal 117 to seal hermetically on the top of the synthesis reaction vessel holder 118. An electronically controlled gas pressure regulator system comprised of pressure regulator 101, gas flow control valve 107, electronic gas pressure regulator 108 and a low-pressure gas flow control valve 110 introduce a protocol selectable, known, reproducible gas pressure to the sealable synthesis reaction vessel inlet chamber 115 and the synthesis reaction vessel inlets 116.

Electronically controlled gas pressure regulator 108 has closed loop control and is capable of gas flow up to 2 liters per minute and capable of controlling pressure within 0.02 psi (0.140 kPa) with a maximum output pressure of 1 bar (14.7 psi or 100 kPa). The known, reproducible gas pressure applied to the chamber 115 is selected at a level that will flow the synthesis reagent(s) down through the synthesis media 120 but not high enough to expel any of the synthesis reagent(s) out the reaction vessel(s) outlets 119. Space directly below the synthesis media, the volume of reagent(s) delivered per synthesis reaction vessel, the known, reproducible pressure applied to the reaction vessel inlet(s) 116, the opening size of the reaction vessel outlet(s) 119, the material the reaction vessel(s) are made of and the surface tension of the synthesis reagent(s) with the material of synthesis reaction vessel walls are all selected so that synthesis reagent(s) can be flowed through the synthesis media without being expelled out the synthesis reaction vessel outlet(s) 119. The opening size of the reaction vessel outlets range between 0.05 to 0.18 inch (1.27 to 4.57 mm) and preferentially 0.07 inch (1.78 mm) for wells of a 384-well plate and 0.14 inch (3.56 mm) for individual synthesis reaction vessels. The sealable synthesis reaction vessel inlet chamber 115 containing the synthesis reaction vessel inlet(s) is vented thru valve 111 to release the pressure once the reagent has flowed down through the synthesis media over the time desired. A vacuum generating system, gas pressure regulator 102, electronically controlled pressure regulator 103, vacuum generating gas control valve 104, vacuum generating gas flow rate control needle valve 105, and vacuum generator 106, is connected to the sealable synthesis reaction vessel inlet chamber 115 through valve 111, whereas negative pressure is captured and applied to the synthesis reaction vessel inlet(s) 116. Preferentially, the vacuum generating device is an air powered vacuum Venturi device 106 having a source gas inlet for connection to a source gas, a gas outlet and a vacuum outlet connected to the sealable synthesis reaction vessel inlet chamber 115, whereas the gas source can be any source of inert compressed gas that provides a known, reproducible, and selectable pressure and flow of gas set manually or electronically or using a combination of both. Venturi device 106, driven with gas from an electronically controlled gas pressure regulator 103, offer countless values of negative pressure differentials by simply adjusting the pressure and flow of compressed inert gas through the venturi device 106, whereas controlled and easily reproducible negative pressures are generated in response to flow of pressurized inert gas supplied to Venturi device 106. The vacuum level and the time vacuum to be applied to the synthesis reaction vessel inlet chamber 115, are selectable. At the end of the time that vacuum is applied, the chamber 115, is vented thru valve 111, to stop reverse flow of synthesis reagent(s). The process of flowing reagent forward, then backward and pausing for the reaction to occur is repeated as many times as needed to mix the reagents then it is repeated with pauses included to allow the reaction to occur until the total desired reaction time is reached. To their advantage, Venturi devices 106 are maintenance free and have no moving parts that can wear out or jam. Preferably, the Venturi apparatus 106 supplies negative pressures to the sealable synthesis reaction vessel inlet chamber 115 that range from 0 to negative (−) 2 psi (14 kPa) or lower as appropriate for the synthesis scale of the reaction vessel(s). The resulting pressure differentials were found through experimentation to be strong enough (i.e., when the negative pressure increases to "lower" values, it is meant that the vacuum is getting stronger) to provide reverse flow of liquid reagents in individual synthesis reaction vessel(s) arrayed in a 96-well plate holder, whereas the individual synthesis reaction vessel(s) have synthesis scales ranging from 10 nmol to 20 micromoles in a period of time that is compatible with the short coupling duration currently practiced in nucleic acid synthesis, often 30 to 90 seconds in DNA synthesis, 3 to 12 min in RNA synthesis, and at a rate and pressure that does not generate bubbles through the synthesis media. Useful time to complete a backward flow of liquid synthesis reagent(s) takes from 1 second to 20 seconds, preferably within 2 to 10 seconds. When using a 384-well synthesis plate that have synthesis scales ranging from 2 to 100 nmol per well, negative pressures supplied to the synthesis reaction vessel inlet chamber 115 by the Venturi device that range from negative (−) 0.1 to −0.5 psi (−0.7 to −3.4 kPa), provide a vacuum strong enough to develop backward flow of volumes of synthesis reagent(s) ranging from 5 to 50 μl of liquid synthesis reagent(s) per synthesis reaction vessel(s) ("well"), through all the synthesis reaction vessel(s) of the 384-well synthesis plate. An automated solid phase synthesizer modified with a vacuum Venturi system and selectable, known, reproducible backward pressures can produce bidirectional flow of the invention when operated by the automated solid phase synthesizer control system selecting suitable preset differential pressures levels.

When each synthesis reaction is complete, where synthesis reaction times are known by someone skilled in the art of solid phase synthesis and have been applied according to an automated solid phase synthesizer equipped with bidirectional flow of FIG. 1, spent synthesis reagent(s) are sent to the waste container 123. To accomplish moving the spent synthesis reagent(s) to the waste container 123, the top space 115, containing synthesis reaction vessel inlets 116, of the synthesis reaction vessels 124, is sealed and a high drain gas pressure high enough to move the spent synthesis reagents completely out of the synthesis reaction vessel 124, and to the waste container 123 is applied to the top space 115 while an exit flow path between waste port 121, and the waste container 123, is opened. The high drain gas pressure source supplies a known, selectable, reproducible gas pressure where the high drain pressure level is selected is determined by someone skilled in automated solid phase synthesis and is based on synthesis medium resistance to flow for each specific synthesis reagent. The high drain gas pressure is supplied by electronically controlled gas flow regulator 101 and applied to the top space 115, through a flow path starting with the gas pressure regulator 101 to tube 125, valve 109, tube 126, tube 127, into top space 115. The spent synthesis reagent is expelled out the synthesis reaction vessel outlets 119 through waste exit port 121, tube 122, valve 127, tube 128 and into waste container 123.

FIG. 2 illustrates the embodiment of a bidirectional reaction flow system that can be fitted to synthesizers having bank(s) 227 containing synthesis reaction vessel(s) each containing synthesis medium 207 with their inlet(s) 208, located in a common sealable space 206, and reaction vessel(s) outlet(s) 210, in a separate common sealable space 209, such that all the synthesis reaction vessels contained within a bank 227, flow synthesis reagent(s) through their synthesis medium 207 simultaneously, thus bidirectional synthesis reagent flow is performed simultaneously on all synthesis reaction vessels within each bank 227. The synthesis reaction vessel inlet(s) 208 of each the bank are within a sealable space 206, where the sealable space can be pressurized by a selectable, known, reproducible pressure as well as vented at a selectable, known, reproducible rate and where synthesis reaction vessel outlet(s) 210, of each the bank 227, are within a sealable space 210, where the sealable space 210, can be pressurized by a selectable, known, reproducible pressure as well as vented at a selectable, known, reproducible rate through adjustable needle valve 226, valve 203 and tube 202. When fitting the invention to an automated solid phase synthesizer of the design shown in FIG. 2, all activities described are carried out by the control system of the automated solid phase synthesizer. The invention teaches the operation is as follows, bank inlet sealable door 204 is opened by pneumatic cylinder 231, to unseal inlet space 210 of bank 227. Reagent delivery system of existing solid phase synthesizer can be any suitable design, however in FIG. 2, it is comprised of reagent bottle, bottle to delivery valve connecting tub, delivery valve and synthesis reagent dispense nozzle tube collectively identified as item 201, delivers a volume of one of the synthesis reagents to synthesis reaction vessel inlets 208. After delivery of the synthesis reagent(s), the sealable space 206, containing the inlet(s) of the synthesis reaction vessel(s) 208, is sealed by bank top door 204, and seal 205, then pressurized using a known, reproducible, positive gas pressure the optimal value of which is dependent on volume of the synthesis reagent delivered and the flow characteristics of the synthesis medium 207, and is usually in the range of 0.1 psi to 10 psi (0.7 to 69 kPa). The known pressure is selected to flow the synthesis reagent through the synthesis medium 207, to collect the synthesis reagent below the synthesis medium 207, without exiting the synthesis reaction vessel outlet(s) 210. The known positive gas pressure is produced using electronic controlled gas pressure regulator 224 with closed loop control capable of gas flow up to 2 liters per minute and capable of controlling pressure within 0.02 psi (0.14 kPa) with a maximum output pressure of 1 bar (100 kPa). The known pressure applied to the top space 206, comes from the electronic controlled gas pressure regulator 224, whereas the electronic controlled gas pressure regulator receives gas through its gas in port and from Inert Gas In through tube 223, and is applied to bank 227, top space 206, from the regulator 224 through tube 229, through valve 225, through tube 221, through valve 203, and through tube 202. The optimal time and gas pressure needed to complete movement of the synthesis reagent(s) through the synthesis medium 207, is based on the volume of the synthesis reagent(s), the viscosity of the synthesis reagent(s) and the resistance of flow through the synthesis medium 207. The exact time and gas pressure used for flowing each synthesis reagent through the synthesis medium is arrived at by experimentation of someone skilled in the art of automated solid phase synthesis. Upon completion of moving the synthesis reagent to the space below the synthesis medium 228, which is within each synthesis reaction vessel 230, the bank top space 206, is vented, and the bank bottom space 209, is sealed, and a known, reproducible positive gas pressure is applied to the bank bottom space 209 from the electronic pressure regulator 224 through tube 218, valve 213, tube 214, valve 212 and tube 211. The synthesis reagent contained in the synthesis reaction vessel(s) flows backward through the synthesis medium 207, for a predetermined time such that the space under the synthesis medium 207, is void of the synthesis reagent(s). The bank bottom space 209, is vented through tube 211, valve 212, tube 214, valve 213, tube 232 and adjustable needle valve 217 where the vent rate is determined by pre-setting the adjustable needle valve 217. After venting bank bottom space 209, a selectable, known, reproducible pressure is applied to bank top space to repeat the bidirectional flow cycle. The automated solid phase synthesizer controller and protocol is used to define timing and frequency of bidirectional flow based on known reaction time.

When each synthesis reaction is complete, where synthesis reaction times are known by someone skilled in the art of solid phase synthesis and have been applied according to an automated solid phase synthesizer equipped with bidirectional flow of FIG. 2, spent synthesis reagent(s) are sent to the waste container 216. To accomplish moving the spent synthesis reagent(s) to the waste container 216, the top space 206, of the synthesis reaction vessels 230, is sealed and a high drain gas pressure high enough to move the spent synthesis reagents completely out of the synthesis reaction vessel 230, and to the waste container 216 is applied to the top space 206, of the bank 227, while an exit flow path between bank outlet 234, and the waste container 216, is opened. The high drain gas pressure source supplies a known, selectable, reproducible gas pressure where the high drain pressure level is selected is determined by someone skilled in automated solid phase synthesis and is based on synthesis medium resistance to flow for each specific synthesis reagent. The high drain gas pressure is supplied by electronically controlled gas pressure regulator 219 whereas gas pressure regulator 219 receives gas pressure from Inert Gas In through tube 222, and applied to the top bank space 206, through a flow path starting with the electronically controlled gas pressure regulator 219 to tube 233, valve 220, tube 221, valve 203, tube 202, through top door 204, into top bank space 206. The spent synthesis reagent is expelled out the bank outlet 234 of the bank 227, through tube 211, valve 212 and tube 215 to waste container 216.

FIG. 3 illustrates the embodiment of a bidirectional synthesis reaction vessel flow system which can be incorporated into an automated solid phase synthesizer having support and control systems able to operate individual and independently sealable synthesis reaction vessel(s) 305, where the individual synthesis reaction vessel(s) 305, has a top opening 329, and where said top opening 329 can be closed and sealed by pneumatic cylinder 303, door 304 and O-ring seal 306, as needed to perform bidirectional synthesis reagent flow through synthesis medium 307, independently from each other. The invention teaches that the individual synthesis reaction vessel(s) 327, have independent sealable inlet(s) 329, and separate independent sealable outlet(s) 309. In addition, the invention teaches that each individual synthesis reaction vessel can receive positive pressure as well as vent to its inlet 329, and independently to its outlet 309, to effect bidirectional flow of the invention for moving synthesis reagent(s) through synthesis medium 307, held in synthesis reaction vessels 327.

When fitting the invention to an automated solid phase synthesizer of the design as shown in FIG. 3, all activities described are carried out by the control system of the automated solid phase synthesizer. After the automated solid phase synthesizer delivers the synthesis reagent(s) to the synthesis reaction vessel(s) 327, using example synthesis reagent delivery system of the automated solid phase synthesizer represented in FIG. 3 by components identified as 301, the sealable inlet 329 of the synthesis reaction vessel 327 is vented via adjustable needle valve 325, through valve 326, and tube 302, when the top of the synthesis reaction vessel needs to be vented and the sealable outlet 309 of the synthesis reaction vessel(s) 327 is vented through tube 310, valve 311, tube 314, valve 315, tube 331, and adjustable needle valve 316 where the adjustable needle valve 316, is preset to slow the flow rate causing a slight pressure to build in the bottom space 328, of the synthesis reaction vessel 327, so that synthesis reagent within the space under the synthesis medium 328, which results in the synthesis reagent(s) being retained in bottom space 328, under the synthesis medium 307, and not exiting the synthesis reaction vessel 327, out outlet 309. Sealable inlet 329, of the synthesis reaction vessel 327, is sealed using top door 304, seal 306, which is operated by pneumatic cylinder 303. The sealable inlet(s) 329, of the synthesis reaction vessel(s) 327, is pressurized using a selectable, known, reproducible, positive gas pressure the optimal value of which is dependent on volume of the synthesis reagent delivered, flow setting of adjustable needle valve 316 and the flow characteristics of the synthesis medium 307, and is usually in the range of 0.1 psi to 10 psi (0.7 to 69 kPa) to move the synthesis reagent through the synthesis medium 307, to the bottom space 328, of the synthesis reaction vessel 327. The known positive gas pressure is produced using electronic controlled gas pressure regulators 320, and is applied to the inlet 329, of the synthesis reaction vessel 327, whereas electronically controlled gas pressure regulator 320 has a closed loop control capable of gas flow up to 2 liters per minute or more for larger synthesis scales and capable of controlling pressure within 0.02 psi (0.14 kPa) with a maximum output pressure of 1 bar (100 kPa). The optimal time and gas pressure needed to complete movement of the synthesis reagent(s) through the synthesis medium 307, is based on the volume of the synthesis reagent(s), the viscosity of the synthesis reagent(s) and the resistance of flow through the synthesis medium 307. The exact time and gas pressure used for movement of each synthesis reagent through the synthesis medium is arrived at by experimentation of someone skilled in the art of automated solid phase synthesis and is determined by observation. The selectable, known, reproducible, gas pressure is applied to the top 329 of the synthesis reaction vessels 327, starting with Gas IN from tube 319, through low pressure electronic regulator 320, through tube 332, valve 323, tube 324, valve 326, and tube 302, upon completion of flowing the synthesis reagent to the bottom space 328 of the synthesis reaction vessel 327, the top space 305 of the synthesis reaction vessel 327 is sealed by valve 326 being ON and valves 323 and 322 being OFF. A known, selectable, reproducible positive gas pressure is applied to the outlet 309, of the synthesis reaction vessel 327 from the electronically controlled gas pressure regulator 320, through tube 317, valve 315, tube 314, valve 311 and tube 310. The synthesis reagent contained in the synthesis reaction vessel 327, flows backward up through the synthesis medium 307, until the pressure in the top space 305, of the synthesis reaction vessel 327, that is trapped on top of the synthesis reaction reagent equals the selectable, known, reproducible, gas pressure applied to the synthesis reaction vessel outlet 309. At such time that it is desired to flow the synthesis reagent from the top space 305, of synthesis reaction vessel 327, down through the synthesis medium 307, to the bottom space 328, of the synthesis reaction vessel 327, the selectable, known, reproducible gas pressure applied to the outlet 309, of the synthesis reaction vessel 327, is turned OFF and a vent is applied to the outlet 309, of the synthesis reaction vessel. For chemistry reactions that benefit from a constant flow rate of the synthesis reagent(s) through the synthesis medium 307, the vent rate is defined by the flow rate of adjustable needle valve 316, following an exit path from outlet 309 of the synthesis reaction vessel 327, through tube 310, valve 311, tube 314, valve 315 and the adjustable needle valve 316. For chemistry reactions that benefit from longer flow rate time, such as coupling, thus maintaining the synthesis reagent(s) in contact with the synthesis medium 307, for a longer time, a selectable, know, reproducible gas pressure is stepped down over time is applied to the outlet 309 of the synthesis reaction vessel 327. The selectable, known, reproducible, gas pressure is supplied by the electronic controlled gas flow regulator 320, and is applied to the outlet 309 of the synthesis reaction vessel 327, through flow path tube 310, valve 311, tube 314, valve 315, tube 327, and the regulator 320.

Upon venting the synthesis reaction vessel outlet 309, the synthesis reagent(s) located in the top 305 of the synthesis reaction vessel 327, are moved back toward the outlet 309, of the synthesis reaction vessel 327. Upon the synthesis reagent(s) reaching the space under the synthesis media 328, the process of moving the synthesis reagent(s) backward through the synthesis medium 307, and down again can be repeated as needed.

When each synthesis reaction is complete, where synthesis reaction times are known by someone skilled in the art of solid phase synthesis and have been applied according to an automated solid phase synthesizer equipped with bidirectional flow of FIG. 3, spent synthesis reagent(s) are sent to the waste container 313. To accomplish moving the spent synthesis reagent(s) to the waste container 313, inlet 329 of the synthesis reaction vessel 327 is sealed and a high drain pressure high enough to move the spent reagents completely out of the synthesis reaction vessel 327, and to the waste container 313 is applied to the top space 329 of the synthesis reaction vessel 327, while an exit flow path between the outlet 309 of the synthesis reaction vessel 327 and the waste container 313, is opened. The high drain gas pressure source supplies a known, selectable, reproducible gas pressure where the high drain pressure level is selected is determined by someone skilled in automated solid phase synthesis and is based on synthesis medium resistance to flow for each specific synthesis reagent. The high drain gas pressure is supplied from Inert Gas In through tube 318, by electronically controlled gas pressure regulator 321 and is applied to the top space 329 through a flow path starting with the out port of the electronically controlled gas pressure regulator 321 to tube 330, valve 322, tube 324, valve 326, tube 302, through top door 304, into inlet 329 of synthesis reaction vessel 327. The spent synthesis reagent is expelled out the outlet 309 of the synthesis reaction vessel 327, through tube 310, valve 311 and tube 312 to the waste container 313.

Exemplary embodiments of the invention are illustrated herein by the automated solid phase synthesis of nucleic acids using high throughput synthesizer modified with the bidirectional flow systems of the invention.

Nucleic Acid Synthesis Using a Synthesizer Equipped with a Bidirectional Fan-Based Flow System:

20-mer and 21-mer oligonucleotides (192 oligos each) were synthesized with Dr. Oligo 768XLc (Biolytic Lab Performance) using β-cyanoethyl phosphoramidite chemistry and a 384-well synthesis plate holding CPG embedded frits covalently derivatized with 25 nmol of Ionis Universal Linker per well. A bidirectional flow system was added to the synthesizer by connecting two CPU fans (Winsinn Brushless Fan) hermetically sealed in series was connected to the synthesizer's synthesis chambers vent line. A computer program, communicating with valve controllers, motion controllers, pressure controllers, controls reagent dispensing and forward and backward reagent flows, chemical reaction duration, and removal of spent reagents to waste. The fans are connected to an electronic board controlled by the software running the synthesis protocol. The oligonucleotide solid phase synthesis proceeds through cycles, whereas a cycle comprised the following steps: (1) Deblock of dimethoxytrityl protective groups with 3% trichloroacetic acid in dichloromethane (50 µl per reaction vessel (25 sec) then 45 µl per reaction vessel (20 sec)), (2) coupling for 80 sec with 5-ethylthiotetrazole (ETT, 250 mM in acetonitrile, 10 µl per reaction vessel) and dimethoxytrityl-protected deoxynucleotide-phosphoramidite (50 mM in acetonitrile, 10 µl per reaction vessel), (3) oxidation (20 µl per reaction vessel, iodine (20 mM) in tetrahydrofuran/pyridine/water (80/10/10)) for 25 sec and (4) capping using Cap B (12 µl per reaction vessel, 20% N-Methylimidazole in acetonitrile) and Cap A (8 µl per reaction vessel, 20% acetic anhydride in acetonitrile) for 20 sec. Bidirectional flows were used during the coupling steps, whereas forward flow (8 sec) was followed by backward flow (5 sec) and hold (5 sec). Forward, backward and hold steps were repeated until reagents were drained under higher pressure (7 psi; 48 kPa) to waste. Forward flow used a slow pressurization of the synthesis chamber to complement gravity-based flow in all 384-wells while without causing reagent dripping. The slow pressurization was measured to increase the sealed space pressure by 0.2 psi (1.4 kPa) in 20 sec. Turning on the fans for 5 sec generated an outlet air flow of 2.5 L/min, sufficient to generate backward flow of liquid reagents through all 384-wells at a flow rate around 2 to 5 µl/s per well. The volume of coupling reagent (20 µl) is retained in a well without dripping under gravity or under positive pressure differential lower than 0.4 psi (2.8 kPa) and was fully flowed backward through the synthesis medium four times over a coupling step duration. Upon completing the synthesis, the 384-well synthesis plate was deprotected using a one-gallon Biolytic heated pressure chamber containing saturated (28-30%) ammonium hydroxide [300 mL in the chamber, 80° C., 90 min] then desalted with acetonitrile (2×100 µl per reaction vessel). Oligonucleotides were eluted with water (2×50 µl per reaction vessel) in a 384-well collection plate and analyzed. All oligonucleotides were synthesized with high purity (around 90 to 95%), and of correct sequences as inferred by their full-length peak mass spectra (ESI).

Nucleic Acid Synthesis Using Synthesizer Equipped with a Bidirectional Venturi-Based Flow System:

Twelve oligonucleotides (32-mer, 37-mer and 65-mer) were synthesized using conventional phosphoramidite chemistry and Biolytic 100 nmol synthesis columns secured in a plate holder with synthesizer (Dr. Oligo 192 Xlc, Biolytic Lab Performance) equipped with a T style vacuum Venturi (Model VMT0504 from Vacuforce, Indianapolis Ind.) with a perpendicular 6 mm exhaust port that allows to vent gas displaced from the synthesis chambers to a laboratory exhaust hood. The Venturi vacuum system is connected to the synthesis chambers and further comprises a high pressure electronic controlled regulator, a gas flow on and off valve, a needle valve (as an adjunct flow restrictor). The venturi device has a 0.5 mm Venturi nozzle diameter and is connected to a compressed nitrogen supply (60 psi; 410 kPa) and to the synthesis chambers via a 5/32" (4 mm) size supply port and vacuum port, respectively. The high pressure electronic controlled regulator allows selection of a variety of gas flow rates to the venturi which in turn varies the vacuum level applied in the sealed synthesis chambers. The VMT0504 venturi vacuum device generates outlet air flow ranging from 0 to 11.4 L/min creating negative pressures in the synthesis chambers ranging from 0 to negative (–) 2 psi (–14 kPa) as measured by compound pressure gauge. The negative pressure applied to the synthesis chamber was set at –0.24 psi (–1.65 kPa), which is sufficient to generate backward flows in the Biolytic synthesis columns. It is to be noted that the gravity flow rate of acetonitrile (ACN) through the 100 nmol columns is around 100 µl/min/reaction vessel. Holding to –0.24 psi (–1.65 kPa) pressure differential for 1 to 5 sec is enough to flow reagents through the synthesis frits at a flow rate around 5 to 10 µl/s/reaction vessel, depending on the reagent viscosities. The 192 XLc synthesizer is further equipped with low pressure electronic regulators that allow very low pressures, down to 0.02 psi (0.14 kPa), to pressurize the top of the synthesis chambers allowing for controlled forward flows of liquid reagents through the synthesis reaction vessels. A positive pressure differential of 0.4 psi (2.8 kPa) was selected to allow forward flow of the coupling reagents in all reaction vessels, without causing the coupling reagents to exit the reaction vessels. Coupling of 2'-deoxynucleotide phosphoramidites in acetonitrile (50 mM, 40 µl per reaction vessel) activated with ETT in acetonitrile (250 mM, 40 µl per reaction vessel) is carried out for 60 sec/cycle by alternating forward and backward flows. Trityl groups were cleaved with 3% trichloroacetic acid in dichloromethane (2×85 µl per reaction vessel; 2×30 sec). Capping was carried out for 30 sec by delivering successively Cap B (55 µl, 20% N-methylimidazole in tetrahydrofuran per reaction vessel) and Cap A (45 µl, 20% acetic anhydride in tetrahydrofuran per reaction vessel). Oxidation was carried out for 30 sec using a 20 mM iodine solution (80 µl, THF/Pyridine/water: 80/10/10 per reaction vessel). Upon completing the synthesis, support bound oligonucleotides were treated with 10% triethylamine in ACN (2×75 µl per reaction vessel for 8 min), washed with ACN then cleaved and deprotected in the gas phase using a heated pressure chamber containing a solution of saturated ammonium hydroxide (28-30%, 300 mL total volume in the heated pressure chamber, 80° C., 90 min). Upon cooling, reaction columns were washed with ACN (2×150 µl per reaction vessel) then each oligonucleotide was eluted with water containing 50% acetonitrile and analyzed by mass spectroscopy. Oligonucleotides were of correct sequences as inferred by their full-length peak mass with crude purity ranging from 92.8 to 97.5% (32-mer), 93.5 to 97.8% (37-mer) and 80.5 to 89% (65-mer).

What is claimed is:

1. A bidirectional flow reaction system for solid phase synthesis, comprising one or more generators of gas pressure differential across opposite ends of at least one reaction vessel containing porous, solid synthesis media and a liquid reagent having been introduced thereto, the liquid reagent having reactants that react with active sites of the synthesis media while in contact with the active sites, alternating net gas pressure differential relative to a zero-flow equilibrium pressure differential yielding a reproducible bidirectional flow of liquid reagent through the synthesis media that keeps the liquid reagent within the reaction vessel and maintains contact between reactants and active sites for a specified time duration,
　　wherein the at least one reaction vessel has at least one valve at one end thereof which is alternately connectable to one of the generators of net gas pressure differential and to a vent open to atmospheric pressure to yield the alternating net gas pressure differential.

2. The bidirectional flow reaction system as in claim 1, wherein a positive gas pressure differential yields a forward flow of liquid reagent through the synthesis media while a negative gas pressure differential yields a backward flow of liquid reagent through the synthesis media.

3. The bidirectional flow reaction system as in claim 1, wherein gas pressure is a positive pressure at both ends of the reaction vessel, one positive pressure being greater than the other, the reaction vessel having at least one valve connected at its higher-pressure end to alternately receive high pressure gas from a gas source and vent the gas pressure to atmosphere.

4. The bidirectional flow reaction system as in claim 1, wherein gas pressure is a negative pressure at both ends of the reaction vessel, one negative pressure being a greater reduction below atmospheric pressure than the other, the reaction vessel having at least one valve and a vacuum generator connected at its lower-pressure end to alternately open to atmosphere and decrease gas pressure.

5. The bidirectional flow reaction system as in claim 1, wherein at least one end of the reaction vessel is coupled to a vacuum generator.

6. The bidirectional flow reaction system as in claim 5, wherein the vacuum generator is a Venturi vacuum generator.

7. The bidirectional flow reaction system as in claim 5, wherein the vacuum generator is a set of one or more fans in a sealed gas flow path leading to the reaction vessel.

8. The bidirectional flow reaction system as in claim 5, wherein the vacuum generator is a pneumatic cylinder with piston.

9. The bidirectional flow reaction system as in claim 1, wherein the gas pressure differential is in a range from 0.1 to 10 psi (0.7 to 69 kPa).

10. The bidirectional flow reaction system as in claim 1, wherein the gas pressure differential is applied for a time duration in a range from 1 to 20 seconds.

11. The bidirectional flow reaction system as in claim 1, wherein a varying gas pressure differential yields a varying flow of liquid reagent through the synthesis media without the liquid reagent being expelled from the reaction vessel.

12. The bidirectional flow reaction system as in claim 11, wherein the variable flow of liquid reagent is an alternately forward and backward movement through the solid synthesis media.

13. The bidirectional flow reaction system as in claim 11, wherein the variable flow of liquid reagent is in a range from 10 microliters per second to 10 liters per minute per reaction vessel.

14. The bidirectional flow reaction system as in claim 1, wherein the reaction vessel is in the form of a multi-well high-density plate or holder that contains at least one reaction vessel.

15. The bidirectional flow reaction system as in claim 14, wherein the variable flow of liquid reagent is in a range from 1 to 10 microliters per second per well.

16. A bidirectional flow reaction system for solid phase synthesis, comprising one or more generators of positive as well as negative gas pressure differential across opposite ends of at least one reaction vessel containing porous, solid synthesis media and a liquid reagent having been introduced thereto, the liquid reagent having reactants that react with active sites of the synthesis media while in contact with the active sites, the positive as well as negative gas pressure differential yielding a reproducible bidirectional flow of liquid reagent through the synthesis media that keeps the liquid reagent within the reaction vessel and maintains contact between reactants and active sites for a specified time duration,
　　wherein the gas pressure differential is created by applying a pressure at a first end of the reaction vessel having at least one valve and an opposite end of the reaction vessel being open to atmospheric pressure.

17. The bidirectional flow reaction system as in claim 16, wherein the first end has at least one valve and is alternately connected to a high-pressure gas source and vented to atmosphere.

18. The bidirectional flow reaction system as in claim 16, wherein the first end has at least one valve and is alternately connected to a vacuum generator and vented to atmosphere.

19. A bidirectional flow reaction system for solid phase synthesis, comprising one or more generators of positive as well as negative gas pressure differential across opposite ends of at least one reaction vessel containing porous, solid synthesis media and a liquid reagent having been introduced thereto, the liquid reagent having reactants that react with active sites of the synthesis media while in contact with the active sites, the positive as well as negative gas pressure differential yielding a reproducible bidirectional flow of liquid reagent through the synthesis media that keeps the liquid reagent within the reaction vessel and maintains contact between reactants and active sites for a specified time duration,
　　wherein a first end of the reaction vessel has at least one valve and is alternately connected to a high-pressure gas source and vented to atmosphere, the gas pressure initially creating a positive gas differential by applying a pressure from the gas source at the first end of the reaction vessel and an opposite end of the reaction vessel is closed so pressure builds in said second end of reaction vessel until pressure is equal in both ends of the reaction vessel, and whereas when connected to atmospheric pressure built up pressure in the closed end pushes reagent in the opposite direction until pressure at both ends are again equal.

20. A method of controlling bidirectional flow of reagent through a reaction vessel, comprising:
　　introducing a liquid reagent into at least one reaction vessel containing a solid synthesis media, the liquid reagent having reactants that react with active sites of the synthesis media while in contact with the active sites; and
　　generating a reversing gas pressure differential across opposite ends of the at least one reaction vessel, the reversing gas pressure differential yielding an alternating forward and backward flow of reproducible volumes of liquid reagent through the synthesis media that keeps the liquid reagent within the reaction vessel and maintains contact between reactants and active sites for a specified time duration,
　　wherein the reversible gas pressure differential across opposite ends of the at least one reaction vessel is created by alternately applying a net gas pressure and a controlled venting to atmospheric pressure at one end of the reaction vessel, the opposite end of the reaction vessel being sealed, the applying of the net gas pressure producing a reagent flow through the synthesis media from a higher pressure end to a lower pressure end of the reaction vessel until a pressure equilibrium is reached with the sealed end, the controlled venting to atmospheric pressure then producing a reverse reagent flow through the synthesis media until a pressure equilibrium is again reached.

21. The method as in claim 20, wherein the gas pressure initially creates a net positive gas pressure differential by applying a positive gas pressure at a first end of the reaction vessel and an opposite second end of the reaction vessel is closed so pressure builds in said second end of reaction vessel until pressure is equal in both ends of the reaction vessel.

22. The method as in claim 21, wherein the first end is alternately connected to a high-pressure gas source and vented to atmosphere, whereas when the first end is connected to atmospheric pressure built up in the closed second end pushes reagent in the opposite direction until pressure at both ends are equal.

\* \* \* \* \*